United States Patent [19]

Tominaga et al.

[11] Patent Number: 4,593,035
[45] Date of Patent: Jun. 3, 1986

[54] CARBOSTYRIL DERIVATIVES

[75] Inventors: Michiaki Tominaga; Hidenori Ogawa; Takafumi Fujioka; Yung-hsiung Yang; Kazuyuki Nakagawa, all of Tokushima, Japan

[73] Assignee: Otsuka Pharmaceutical Company Limited, Tokyo, Japan

[21] Appl. No.: 679,632

[22] Filed: Dec. 10, 1984

[30] Foreign Application Priority Data

Dec. 14, 1983 [JP] Japan ................... 58-235863

[51] Int. Cl.⁴ ................ A61K 31/47; C07D 215/38
[52] U.S. Cl. ........................... 514/312; 546/158
[58] Field of Search ............... 546/158; 424/258

[56] References Cited

U.S. PATENT DOCUMENTS 4,415,572 11/1983 Tominaga ................... 424/250

OTHER PUBLICATIONS

Otsuka-CA 95:150468j.
Ueda, CA 33:7797⁹.
Ueda, CA 49:12470ᶜ.

Primary Examiner—Donald G. Daus
Assistant Examiner—Robert Benson
Attorney, Agent, or Firm—Wegner & Bretschneider

[57] ABSTRACT

Novel carbostyril derivatives of the formula:

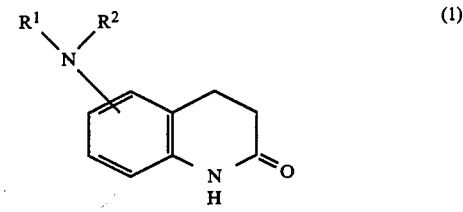

(1)

wherein $R^1$ is hydrogen atom or a lower alkyl group, $R^2$ is a lower alkyl group or a group of the formula:

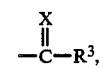

$R^3$ is a lower alkylthio group, a lower alkyl group, a lower alkoxy group, phenoxy group, a phenyl(lower)alkoxy group, a lower alkenyloxy group, a phenyl group which may have a substituent selected from a lower alkoxy and a lower alkylenedioxy group on the phenyl ring, or a group of the formula: $-NR^4R^5$ ($R^4$ and $R^5$ are the same or different and are each hydrogen atom or a lower alkyl group), and X is oxygen atom or sulfur atom, provided that when $R^1$ is hydrogen atom and $R^2$ is the group of the formula:

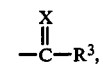

X is not oxygen atom and $R^3$ is not a lower alkyl group, and a pharmaceutically acceptable salt thereof, which show excellent pharmacological activities, such as myocardial contract increasing activity and coronary blood flow increasing activity and are useful for the treatment of heart diseases such as congestive heart failure.

17 Claims, No Drawings

CARBOSTYRIL DERIVATIVES

The present invention relates to novel carbostyril derivatives, more particularly, carbostyril derivatives of the formula:

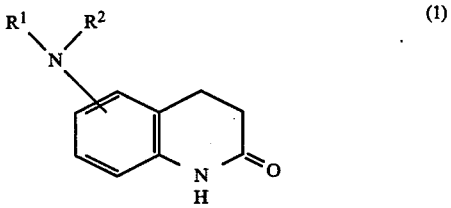

wherein $R^1$ is hydrogen atom or a lower alkyl group, $R^2$ is a lower alkyl group or a group of the formula:

$R^3$ is a lower alkylthio group, a lower alkyl group, a lower alkoxy group, phenoxy group, a phenyl(lower)alkoxy group, a lower alkenyloxy group, a phenyl group which may have a substituent selected from a lower alkoxy and a lower alkylenedioxy group on the phenyl ring, or a group of the formula: $-NR^4R^5$ ($R^4$ and $R^5$ are the same or different and are each hydrogen atom or a lower alkyl group), and X is oxygen atom or sulfur atom, provided that when $R^1$ is hydrogen atom and $R^2$ is the group of the formula:

X is not oxygen atom and $R^3$ is not a lower alkyl group.

The compounds (1) of the present invention show excellent pharmacological activities, such as myocardial contract increasing activity (i.e. positive inotropic activity) and coronary blood flow increasing activity, and hence are useful as cardiotonics for the treatment of heart diseases such as congestive heart failure. The compounds of the present invention are characterized in that they cause no or little increase of cardiac pulse. Moreover, the compounds of the present invention have also hypotension activity and hence are also useful as a hypotension agent. The compounds of the present invention are also characterized in displaying sustained activities for a long period of time and further in having extremely low toxicity.

Each groups in the compounds of the formula (1) include specifically the following groups.

"Lower alkyl group" includes straight or branched chain alkyl groups having 1 to 6 carbon atoms, such as methyl, ethyl, propyl, isopropyl, butyl, isobutyl, tert-butyl, pentyl, hexyl, or the like. "Lower alkylthio group" includes straight or branched chain alkylthio groups having 1 to 6 carbon atoms, such as methylthio, ethylthio, propylthio, isopropylthio, butylthio, isobutylthio, tert-butylthio, pentylthio, hexylthio, or the like. "Lower alkoxy group" includes straight or branched chain alkoxy groups having 1 to 6 carbon atoms, such as methoxy, ethoxy, propoxy, isopropoxy, butoxy, isobutoxy, tert-butoxy, pentyloxy, hexyloxy, or the like.

"Phenyl(lower)alkoxy group" includes phenylalkoxy groups wherein the alkoxy moiety is a straight or branched chain alkoxy having 1 to 6 carbon atoms, such as phenylmethoxy, 2-phenylethoxy, 1-phenylethoxy, 3-phenylpropoxy, 4-phenylbutoxy, 1,1-dimethyl-2-phenyl-ethoxy, 5-phenylpentyloxy, 6-phenylhexyloxy, 2-methyl-3-phenylpropoxy, or the like.

"Lower alkenyloxy group" includes straight or branched chain alkenyloxy groups having 2 to 6 carbon atoms, such as vinyloxy, allyloxy, 2-butenyloxy, 3-butenyloxy, 1-methylallyloxy, 2-pentenyloxy, 2-hexenyloxy, or the like. "Lower alkylenedioxy group" includes straight or branched chain alkylenedioxy groups having 1 to 4 carbon atoms, such as methylenedioxy, ethylenedioxy, trimethylenedioxy, tetramethylenedioxy, or the like.

"Phenyl group which may have a substituent selected from a lower alkoxy or lower alkylenedioxy group on the phenyl ring" includes phenyl groups which may have a substituent selected from a straight or branched chain alkoxy having 1 to 6 carbon atoms and a straight or branched chain alkylenedioxy group having 1 to 4 carbon atoms on the phenyl ring, such as phenyl, 2-, 3- or 4-methoxyphenyl, 2-, 3- or 4-ethoxyphenyl, 3-propoxyphenyl, 4-isopropoxyphenyl, 3-butoxyphenyl, 2-pentyloxyphenyl, 4-tert-butoxyphenyl, 4-hexyloxyphenyl, 3,4-methylenedioxyphenyl, 3,4-ethylenedioxyphenyl, 2,3-methylenedioxyphenyl, 2,3-trimethylenedioxyphenyl, 3,4-tetramethylenedioxyphenyl, or the like.

The carbostyril derivatives (1) of the present invention can be prepared by various processes, for example, by the processes as shown in the following reaction schemes I to VI.

Reaction Scheme-I

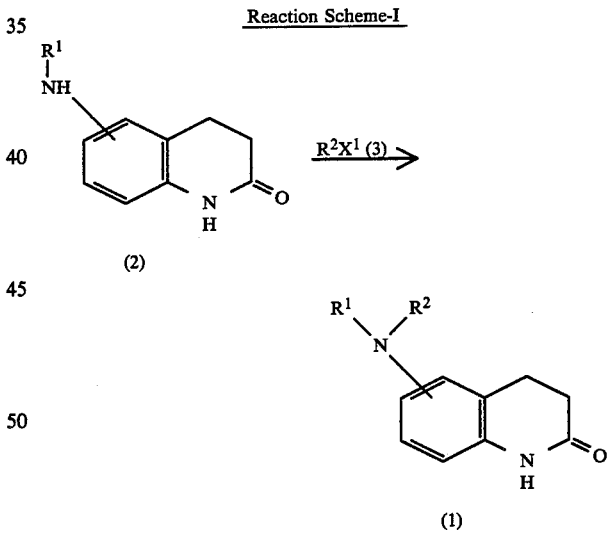

wherein $R^1$ and $R^2$ are the same as defined above, and $X^1$ is a halogen atom such as chlorine, bromine, or iodine.

In the above reaction scheme, the starting compounds of the formula (2) and (3) are known compounds, and the reaction of the compounds (2) and (3) is carried out in an appropriate solvent, preferably in the presence of a basic compound. The basic compound includes organic bases such as triethylamine, trimethylamine, pyridine, dimethylaniline, N-methylmorpholine, 1,5-diazabicyclo[4.3.0]nonene-5 (DBN), 1,8-diazabicyclo[5.4.0]undecene-7 (DBU), 1,4-diazabicyclo[2.2.2]octane (DABCO), or the like, and inorganic bases such as potassium carbonate, sodium carbonate, sodium hydrogen carbonate, potassium hydrogen carbonate, sodium hydroxide, potassium hydroxide, sodium hydride, potassium hydride, or the like. These basic compounds are used in an amount of at least one mole, usually one to three moles, to one mole of the compound (2). The solvent used in the above reaction includes halogenated hydrocarbons such as methylene chloride, chloroform, dichloroethane, etc.; aromatic hydrocarbons such as benzene, toluene, xylene, etc.; ethers such as diethyl ether, tetrahydrofuran, dimethoxyethane, etc.; esters such as methyl acetate, ethyl acetate, etc.; aprotic polar solvents such as N,N-dimethylformamide, dimethylsulfoxide, hexamethylphosphoric acid triamide, etc.; alcohols such as methanol, ethanol, propanol, butanol, 3-methoxybutanol, ethyl cellosolve, methyl cellosolve, etc.; pyridine; acetone; or the like.

The molar ratio of the compound (2) to the compound (3) is not critical but the former is used in an amount of at least one mole, preferably 1 to 1/5 moles, to one mole of the latter. The reaction is usually carried out at a temperature of −20° to 180° C., preferably 0° to 150° C., for 5 minutes to 30 hours.

Reaction Scheme-II

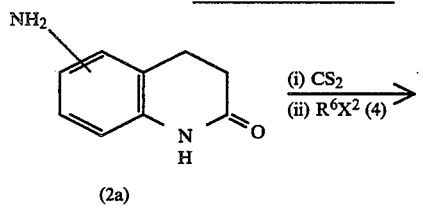

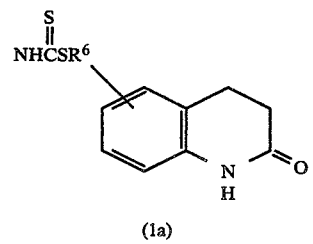

wherein $R^6$ is a lower alkyl group and $X^2$ is a halogen atom such as chlorine, bromine, or iodine.

In the above reaction scheme, the compound (2a) is reacted with carbon disulfide and the compound (4) in an appropriate solvent, preferably in the presence of a basic compound. The basic compound includes the same basic compounds as mentioned hereinbefore as to the reaction scheme-I and is used in an amount of at least one mole, preferably 1 to 1.5 mole, to one mole of the compound (2a). The solvent includes also the same solvents as mentioned hereinbefore as to the reaction scheme-I.

The reaction may be carried out by firstly reacting the compound (2a) with carbon disulfide and then with the compound (4) or by reacting simultaneously the compound (2a) with carbon disulfide and the compound (4). The carbon disulfide and the compound (4) are each used in an amount of at least one mole, preferably 1 to 1.5 mole, to one mole of the compound (2a). The reaction is usually carried out at a temperature of −20° to 150° C., preferably 0° to 100° C., for 30 minutes to 5 hours.

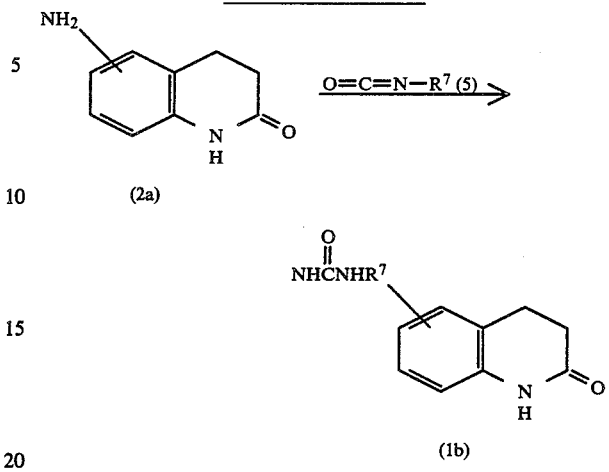

wherein $R^7$ is a lower alkyl group.

In the above reaction scheme, the compound (2a) is reacted with the compound (5) in an appropriate solvent in the presence or absence of a basic compound. The basic compound and the solvent include the same basic compounds and solvents as mentioned hereinbefore as to the reaction scheme-I. The basic compounds are used in an amount of at least one mole, preferably 1 to 1.5 mole, to one mole of the compound (2a). The compound (5) is used in an amount of at least one mole, preferably 1 to 2 mole, to one mole of the compound (2a).

The reaction is usually carried out at a temperature of 0° to 150° C., preferably 0° to 100° C., for 30 minutes to 5 hours.

Reaction Scheme-IV

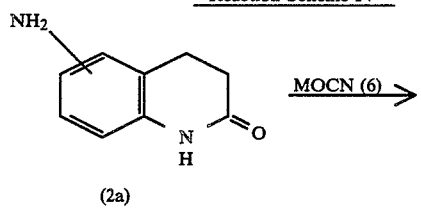

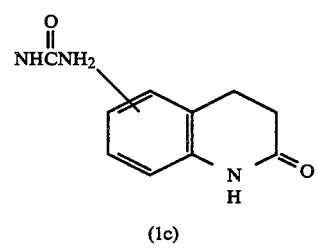

wherein M is an alkali metal such as sodium or potassium.

In the above reaction scheme, the compound (2a) is reacted with the compound (6) in an appropriate solvent in the presence of an acid catalyst. The solvent include acetic acid, water, etc. in addition to the same solvents as mentioned hereinbefore as to the reaction scheme-I. These solvents may be used alone or in combination of two or more thereof. The compound (6) is used in an amount of 1 to 10 moles, preferably 1 to 5 moles, to one mole of the compound (2a). The acid catalyst includes mineral acids such as hydrochloric acid, hydrobromic acid, sulfuric acid, etc., and organic acids such as acetic acid, etc., and is usually used in an amount of 1 to 5 moles to 1 mole of the compound (2a).

The reaction is usually carried out at a temperature of 0° to 150° C., preferably 0° to 100° C., for 10 minutes to 5 hours.

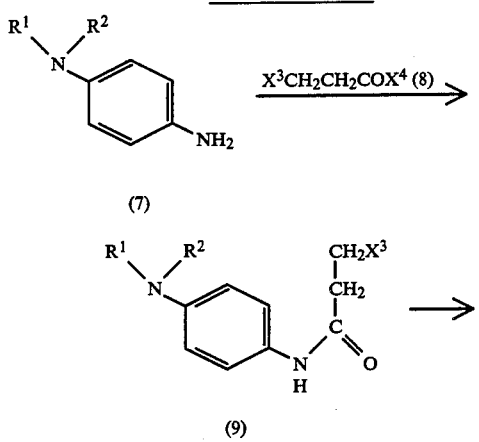

and the same solvents as mentioned hereinbefore as to the reaction scheme-I.

The cyclization reaction of the compound (9) is carried out by so-called Friedel-Crafts reaction and is usually carried out in the presence or absence of a solvent and in the presence of a Lewis acid. The solvent includes all solvents that are usually used in such a reaction, for example, carbon disulfide, nitrobenzene, chlorobenzene, dichloromethane, dichloroethane, trichloroethane, tetrachloroethane, or the like. Lewis acid also includes all acids which are usually used in such a reaction, for example, aluminum chloride, zinc chloride, iron chloride, tin chloride, boron tribromide, boron trifluoride, conc. sulfuric acid, or the like. The amount of Lewis acid is not critical but is usually in the range of 2 to 6 moles, preferably 3 to 4 moles, to 1 mole of the compound (9). The reaction temperature is usually in the range of 20° to 250° C., preferably 40° to 200° C. The reaction time may vary depending on the kinds of the starting materials and catalysts, reaction temperature, or the like, but is usually in the range of 0.5 to 6 hours. When the reaction is carried out in the absence of a solvent, it is advantageous to carry out the reaction in the presence of an inorganic salt such as potassium chloride, sodium chloride, etc.

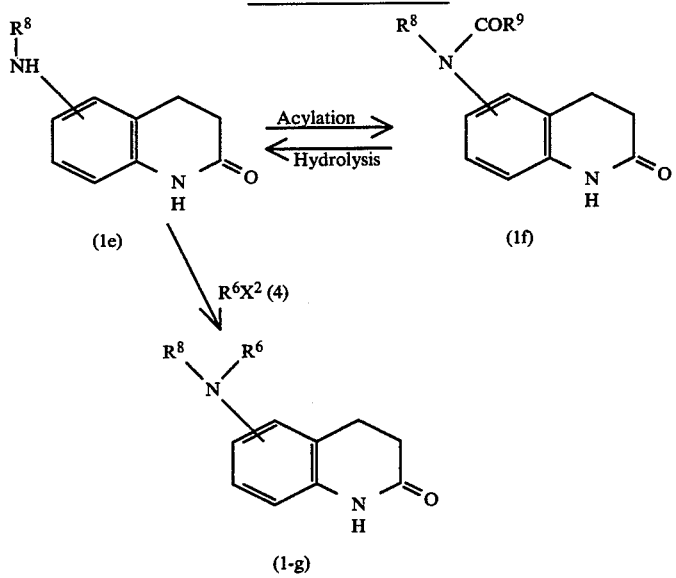

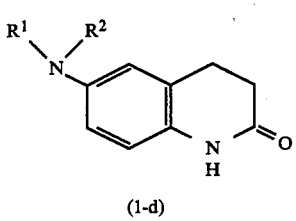

wherein $R^1$ and $R^2$ are as defined above, and $X^3$ and $X^4$ are each a halogen atom such as chlorine, bromine, or iodine.

In the above reaction scheme, the compound (7) is reacted with the compound (8) in the same manner as described in the above reaction scheme-I, except that the compound (8) is used in an amount of at least one mole to one mole of the compound (7), preferably in a large excess amount, in a solvent selected from water $R^6$ and $X^2$ are the same as defined above, and $R^8$ and $R^9$ are each a lower alkyl group.

In the above reaction scheme, the acylation of the compound (1e) is carried out with a conventional acylating agent. The acylating agent includes, for example, lower alkanoyl halides such as acetyl chloride, propionyl chloride, etc., lower alkanoic acids such as acetic acid, propionic acid, etc., lower alkanoic anhydrides such as acetic anhydride, etc. When a lower alkanoyl halide is used as the acylating agent, the acylation reaction is carried out under the same conditions as used in the above reaction scheme-I. When a lower alkanoic anhydride is used as the acylating agent, the acylation reaction is carried out in the presence of a basic compound. The basic compound includes, for example, alkali metals such as sodium metal, potassium metal, etc.; hydroxides, carbonates, or bicarbonates of the above alkali metals, and aromatic amine compounds such as pyridine, piperidine, etc. The reaction may proceed either in the presence or absence of a solvent, but is usually carried out in a solvent. Suitable examples of the solvent are ketones such as acetone, methyl ethyl ketone, etc.; ethers such as diethyl ether, dioxane, etc.; aromatic hydrocarbons such as benzene, toluene, xylene, etc.; water; pyridine; or the like. The acylating agent is usually used in an amount of at least 1 mole to 1 mole of the compound (1e) but preferably in an equimolar or largely excess amount. The reaction is usually carried out at a temperature of 0° to 150° C., preferably 0° to 30° C., for 0.5 to 10 hours. When a lower alkanoic acid is used as the acylating agent, the acylating reaction is advantageously carried out by adding a dehydrating agent such as mineral acids (e.g. sulfuric acid, hydrochloride acid, etc.) or sulfonic acids (e.g. p-toluenesulfonic acid, benzenesulfonic acid, ethanesulfonic acid, etc.) and preferably by maintaining the temperature at 50° to 120° C.

Hydrolysis of the compound (1f) is usually carried out in an appropriate solvent in the presence of an acid or a basic compound. The solvent includes, for example, water; lower alcohols such as methanol, ethanol, isopropanol, etc.; ethers such as dioxane, tetrahydrofuran, etc.; or a mixture of two or more thereof. The acid includes, for example, mineral acids such as hydrochloric acid, sulfuric acid, hydrobromic acid, etc., and the basic compound includes, for example, hydroxides of alkali metals or alkaline earth metals such as sodium hydroxide, potassium hydroxide, calcium hydroxide, etc. The reaction is usually carried out at a temperature of room temperature to 150° C., preferably 80° to 120° C., for 1 to 15 hours.

The reaction of the compound (1e) and the compound (4) is carried out under the same conditions as used in the reaction of the compound (2) and the compound (3) in the reaction scheme-I.

The carbostyril derivatives (1) of the present invention can easily be converted into a pharmaceutically acceptable acid addition salt thereof by treating with a pharmaceutically acceptable acid. The acid includes, for example, inorganic acids such as hydrochloride acid, sulfuric acid, phosphoric acid, hydrobromic acid, etc.; and organic acids such as oxalic acid, maleic acid, fumaric acid, malic acid, tartaric acid, citric acid, benzoic acid, etc.

The desired compounds obtained in the above reactions can easily be isolated from the reaction mixture by conventional isolation and purification methods. The isolation methods are, for example, extraction with a solvent, dilution method, recrystallization, column chromatography, preparative thin layer chromatography, or the like.

The compounds of the present invention have optical isomers, and these optical isomers are also included within the present invention.

The compounds (1) of the present invention are used as a medicament usually in the form of a conventional pharmaceutical preparation, which is prepared by using conventional pharmaceutically acceptable carriers or diluents, such as fillers, thickening agents, binding agents, wetting agents, disintegrators, surface active agents, lubricants, and the like. Various types of preparations may be used for medical use in oral or parenteral routes. For oral administration, the preparations include, for example, solid preparations such as tablets, pills, powders, granules, fine granules, capsules, etc., and liquid preparations such as solutions, suspensions, emulsions, etc. For parenteral administration, the preparations include, for example, suppositories and injections (in the form of solutions and suspensions). In the preparation of tablets, there are used conventional carriers which are widely used, for example, excipients such as lactose, sucrose, sodium chloride, glucose, urea, starches, calcium carbonate, kaolin, crystalline cellulose, silicic acid, etc.; binding agents such as water, ethanol, propanol, simple syrup, glucose solution, starch solution, gelatine solution, carboxymethyl cellulose, shellac, methyl cellulose, potassium phosphate, polyvinylpyrrolidone, etc.; disintegrators such as dried starch, sodium arginate, agar powder, laminaran powder, sodium hydrogen carbonate, calcium carbonate, polyoxyethylene sorbitan fatty acid esters, sodium laurylsulfate, stearic acid monoglyceride, starches, lactose, etc.; disintegration inhibitors such as sucrose, stearine, cacao butter, hydrogenated oils, etc.; absorption promoters such as quaternary ammonium bases, sodium laurylsulfate, etc.; humectants such as glycerine, starches, etc.; absorbents such as starches, lactose, kaolin, bentonite, colloidal silicic acid, etc.; lubricants such as purified talc, stearates, boric acid powder, polyethylene glycol, etc.; and the like. The tablets may be coated in usual manner, and include, for example, sugar-coated tablets, gelatine-coated tablets, tablets having enteric coating, tablets having film coating, or double or plural layers tablets. In the preparation of pills, there are used conventional carriers, for example, excipients such as glucose, lactose, starches, cacao butter, hydrogenated vegetable oils, kaolin, talc, etc.; binding agents such as Arabic gum powder, tragacant powder, gelatine, ethanol, etc.; disintegrators such as laminaran, starches, etc. In the preparation of suppositories, there are used conventional carriers, for example, polyethylene glycol, cacao butter, higher alcohols and esters thereof, gelatine, semisynthetic glycerides, etc. In the preparation of injections, the solution or suspension preparation is sterilized and is made isotonic to blood. In the preparation of solutions, emulsions and suspensions, there are used conventional diluents, for example, water, ethyl alcohol, propylene glycol, ethoxylated isostearyl alcohol, polyoxylated isostearyl alcohol, polyoxyethylene sorbitan fatty acid esters, or the like. For making isotonic the preparations, there are used conventional isotonic agents such as sodium chloride, glucose, or glycerine. These liquid preparations may also be incorporated with conventional solubilizers, buffering agents, and local anesthetic agents. The preparations of the present invention may also be incorporated with other conventional additives, such as colorants, preservatives, perfumes, flavors, sweeting agents, and other medicaments.

The compounds (1) of the present invention are contained in the preparations in a wide range of amount, but are usually contained in an amount of 1 to 70% by weight, preferably 1 to 30% by weight, based on the whole weight of the preparations.

The usage of the preparations of the present invention is not specified and is depending on the shapes of preparations, age and sex of patients, severity of diseases, or the like. For instance, in case of tablets, pills, solutions, suspensions, emulsions, granules and capsules, these are usually administered in oral route. The injections are usually intravenously administered as it stands or after being mixed with co-excipients such as glucose or amino acids, and further are administered as it stands in intramuscular, intracutaneous, subcutaneous, or intraperitoneal route. In case of suppository, it is usually administered in intrarectal route.

Dose of the preparations of the present invention may vary depending on the usages, age and sex of patients, severity of diseases and the like, but is usually in the range of about 0.1 to 10 mg/kg of body/day in the amount of the active compounds (1). The active compounds (1) are usually contained in the preparations in an amount of 2 to 200 mg per dosage unit.

The present invention is illustrated by the following reference example, examples and preparations, but should not be construed to be limited thereto.

REFERENCE EXAMPLE 1

To a solution of potassium carbonate (6.7 g) in acetone (20 ml) and water (20 ml) is added 4-amino-N-methylacetanilide (4.0 g), and thereto is further added dropwise 3-bromopropionyl chloride under ice-cooling. After the addition, the mixture is stirred at the same temperature for 30 minutes. The reaction mixture is poured into water, and the resulting precipitate is filtered, washed with water and dried to give 4-(3-bromopropionylamino)-N-methylacetanilide (6.23 g).

EXAMPLE 1

6-Amino-3,4-dihydrocarbostyril (1 g) is suspended in benzene (20 ml), and thereto is added dropwise a solution of N,N-dimethylcarbamoyl chloride (0.86 ml) in benzene (10 ml) at room temperature. The mixture is reacted at 50° C. for 3 hours, and thereto is added triethylamine (0.86 ml), and the mixture is further reacted at 50° to 60° C. for 5 hours. After the reaction, benzene is distilled off under reduced pressure, and water is added to the residue. The resulting precipitate is separated by filtration and washed with water. The crystal thus obtained is purified by silica gel column chromatography (solvent; chloroform:methanol=100:1) and then recrystallized from methanol-diethyl ether to give 6-(3,3-dimethylureido)-3,4-dihydrocarbostyril (0.6 g), as colorless prisms, m.p. 181°–183° C.

Elementary analysis for $C_{12}H_{15}N_3O_2$: Calcd. (%): C,61.79; H,5.19; N,18.01. Found (%): C,61.57; H,5.11; N,17.88.

EXAMPLE 2

6-Amino-3,4-dihydrocarbostyril (60 g) is added to a solution of potassium carbonate (128 g) in water (300 ml) and acetone (300 ml), and thereto is added dropwise ethyl chlorocarbonate (46 ml) with stirring under ice-cooling. After the addition, the mixture is further reacted at the same temperature for 30 minutes. After the reaction, the reaction mixture is poured into water, and the resulting precipitate is separated by filtration, washed with water and further with diethyl ether. After drying, the crystal thus obtained is purified by silica gel column chromatography (solvent; chloroform:methanol=100:1) and then recrystallized from ethanol to give 6-ethoxycarbonylamino-3,4-dihydrocarbostyril (68.5 g), as colorless prisms, m.p. 193°–194° C.

Elementary analysis for $C_{12}H_{14}O_3N_2$: Calcd. (%): C,61.53; H,6.02; N,11.96. Found (%): C,61.70; H,6.00; N,12.08.

EXAMPLES 3 TO 18

In the same manner as described in Examples 1 and 2, various compounds as shown in Table 1 are prepared by using corresponding starting materials.

TABLE 1

| Ex. No. | $R^1$ | $R^2$ | Crystalline form (solvent for recrystallization) | Melting point (°C.) |
|---|---|---|---|---|
| 3 | H | —C(=S)SCH₃ | Yellow needles (methanol) | 203.5–205.0 |
| 4 | H | —C(=O)OCH₃ | Colorless prisms (methanol) | 234–235 |
| 5 | H | —C(=O)OCH₂CH(CH₃)₂ | Colorless prisms (benzene) | 155–157 |
| 6 | H | —C(=O)O—C₆H₅ | Colorless flaks (ethanol) | 175–177 |
| 7 | CH₃ | —C(=O)OC₂H₅ | Colorless needles (ethyl acetate) | 161–162 |
| 8 | CH₃ | —C(=O)OCH₂CH(CH₃)₂ | Colorless prisms (ligroine-benzene) | 112.5–113.5 |
| 9 | CH₃ | —C(=O)OCH₂—C₆H₅ | Colorless prisms (ethanol) | 129–130 |
| 10 | CH₃ | —C(=O)OCH₂CH=CH₂ | Colorless prisms (ethanol-water) | 121–122 |
| 11 | H | —C(=O)NHCH(CH₃)₂ | Colorless prisms (ethanol) | 252–254 |
| 12 | H | —C(=O)—NH₂ | Colorless needles (dimethylformamide-water) | >300 |
| 13 | CH₃ | —C(=O)CH₃ | Colorless prisms (isopropanol) | 219–220 |
| 14 | H | —CH₃ | Colorless prisms (ethyl acetate) | 164–167 |
| 15 | H | —C(=O)—C₆H₅ | Colorless prisms (methanol) | 246–247 |
| 16 | H | —C(=O)—C₆H₄(OCH₃) | Colorless prisms (methanol) | 217–218 |
| 17 | H | —C(=O)—C₆H₃(OCH₂O) | Colorless prisms (methanol) | 230–231 |

TABLE 1-continued

| Ex. No. | R¹ | R² | Crystalline form (solvent for re-crystallization) | Melting point (°C.) |
|---|---|---|---|---|
| 18 | H | $-\overset{S}{\underset{\|\|}{C}}-\underset{}{\bigcirc}\cdot\tfrac{1}{2}H_2O$ | Yellow needles (methanol) | 214–215 |

EXAMPLE 19

Aluminum chloride (174 g), potassium chloride (17.4 g) and sodium chloride (17.4 g) are molten at 180° to 190° C., and thereto is added 4-(3-bromopropionylamino)-N-methylacetanilide (39 g). The mixture is reacted at the same temperature for 2 hours. After the reaction, the reaction mixture is poured into water and the mixture is extracted with chloroform. The extract is washed with water, dried, and then distilled under reduced pressure to remove chloroform. The resulting residue is purified by silica gel column chromatography (solvent; chloroform:ethyl acetate=1:5) and recrystallized from isopropanol to give 6-(N-methyl-N-acetylamino)-3,4-dihydrocarbostyril (8 g), as colorless prisms, m.p. 219°–220° C.

Elementary analysis for $C_{12}H_{14}N_2O_2$: Calcd. (%): C,66.04; H,6.47; N,12.84. Found (%): C,65.98; H,6.47; N,12.96.

EXAMPLE 20

In the same manner as described in Example 19, the compounds of Examples 1 to 12 and 14 to 18 are prepared by using corresponding starting materials.

EXAMPLE 21

To 6-(N-methyl-N-acetylamino)-3,4-dihydrocarbostyril (8 g) is added 20% hydrochloric acid (100 ml), and the mixture is refluxed for 6 hours. After the reaction, the reaction mixture is distilled under reduced pressure, and to the residue is added 1N aqueous sodium hydroxide. The resulting precipitate is separated by filtration, washed with water, dried, and then recrystallized from ethyl acetate to give 6-methylamino-3,4-dihydrocarbostyril (5 g), as colorless prisms, m.p. 164°–167° C.

Elementary analysis for $C_{10}H_{12}N_2O$: Calcd. (%): C,68.16; H,6.86; N,15.90. Found (%): C,67.81; H,6.80; N,16.14.

EXAMPLE 22

6-Amino-3,4-dihydrocarbostyril (1.6 g) is suspended in dry benzene (16 ml), and thereto is added dropwise a solution of isopropyl isocyanate (1.2 ml) in dry benzene (10 ml) with stirring at room temperature. The mixture is reacted at 50° to 60° C. for 3 hours. After the reaction, the resulting precipitate is separated by filtration, purified by silica gel column chromatography (solvent; chloroform:methanol=50:1), and recrystallized from ethanol to give 6-(3-isopropylureido)-3,4-dihydrocarbostyril (1.2 g) as colorless prisms, m.p. 252°–254° C.

Elementary analysis for $C_{13}H_{17}N_3O_2$: Calcd. (%): C,63.14; H,6.93; N,16.99. Found (%): C,63.12; H,7.07; N,16.97.

EXAMPLE 23

6-Amino-3,4-dihydrocarbostyril (1.6 g) is dissolved in a mixture of acetic acid (5 ml) and water (10 ml), and thereto is added dropwise a solution of sodium cyanate (1.3 g) in water (9 ml) with stirring at room temperature. The mixture is stirred at the same temperature for 1 hour. After the reaction, the resulting precipitate is separated by filtration, washed with water, purified by silica gel column chromatography (solvent; chloroform:methanol=50:1), and recrystallized from dimethylformamide-water to give 6-ureido-3,4-dihydrocarbostyril (0.45 g) as colorless needles, m.p. >300° C.

Elementary analysis for $C_{10}H_{11}N_3O_2$: Calcd. (%): C,58.53; H,5.40; N,20.48. Found (%): C,58.63; H,5.20; N,20.57. NMR $\delta(DMSO-d_6)$: 2.22–2.55 (m, 2H), 2.66–2.92 (m, 2H), 5.68 (br. s, 2H), 6.68 (d, 1H, J=9 Hz), 7.08 (dd, 1H, J=9 Hz, 2 Hz), 7.23 (br. s, 1H), 8.29 (br. s, 1H), 9.85 (br. s, 1H).

EXAMPLE 24

To a solution of 6-amino-3,4-dihydrocarbostyril (3.24 g) in dimethylformamide (10 ml) is added 20N aqueous sodium hydroxide (1.2 ml) with stirring at room temperature. To the mixture is further added carbon disulfide (1.57 ml), and the mixture is stirred at the same temperature for 1 hour. To the reaction mixture is added methyl iodide (1.56 ml) under ice-cooling, and the mixture is stirred at the same temperature for 2.5 hours. After the reaction, the reaction mixture is poured into water, and the resulting precipitate is separated by filtration, washed with water, purified by silica gel column chromatography (solvent; chloroform:methanol=100:1), and recrystallized from methanol twice to give methyl (3,4-dihydrocarbostyril-6-yl)-dithiocarbamate (2.0 g) as yellow needles, m.p. 203.5°–205.0° C.

Elementary analysis for $C_{11}H_{12}N_2OS_2$: Calcd. (%): C,52.35; H,4.79; N,11.10. Found (%): C,52.34; H,4.52; N,11.15.

EXAMPLE 25

In the same manner as described in Examples 1,2 and 24, by using appropriate starting materials, there is obtained the following compound.

Methyl(3,4-dihydrocarbostyril-5-yl)dithiocarbamate, colorless needles, m.p. 220°–221° C. (recrystallized from methanol).

Pharmacological Test

The pharmacological activities of the compounds of the present invention were tested as follows:

Method:

Female and male mongrel dogs, weighing 8–13 kg, were anesthetized by intravenous injection of sodium pentobarbital (30 mg/kg). After intravenous injection of sodium heparin (1,000 U/kg), the dogs are killed by bleeding and the heart was taken out. The heart sample comprised mainly papillary muscle and septum of ventricles of heart, and was perfused through a canule inserted into an anteroseptal artery with the blood from the donor dog at a constant perfusion pressure of 100 mmmHg. The donor dog, weighing 18–27 kg, was anesthetized by intravenous injection of sodium pentobarbital (30 mg/kg), and further, sodium heparin (1,000

U/kg) was administered to the dog by intraveous injection.

The papillary muscle was stimulated with square wave at the stimulus pulse duration of 5 msec and the frequency of 120/minute, at 1.5 times voltage (0.5-3 V) using a bipolar electrode. The papillary muscle showed a steady tension of 1.5 g. The tension produced by stimulation of the papillary muscle was measured with a power displacement transducer. The blood flow volume in the anteroseptal artery was measured with a magnetic flow meter. The produced tension and blood flow volume were recorded on an ink-writing oscillograph. The detailed explanation of this experimental test method is disclosed by Endo and Hashimoto (cf. Am. J. Physiol., 218, 1459-1463, 1970).

Test compounds were administered into the artery at a volume of 10 to 30 μl for 4 seconds. The inotropic activity of the test compounds is shown by the change (%) from the produced tension before administration of drug. The activity for effecting the coronary blood flow volume is shown by the absolute change (ml/minute) from the value before the administration of drug.

Results:
The results are shown in Table 2.
Test compounds:
The test compounds are as follows:
1. 6-(N-Methyl-N-acetylamino)-3,4-dihydrocarbostyril
2. 6-(3-Isopropylureido)-3,4-dihydrocarbostyril
3. Methyl(3,4-dihydrocarbostyril-6-yl)dithiocarbamate
4. 6-Methoxycarbonylamino-3,4-dihydrocarbostyril
5. 6-Ethoxycarbonylamino-3,4-dihydrocarbostyril
6. 6-(N-Methyl-N-isobutoxycarbonylamino)-3,4-dihydrocarbostyril
7. 6-Benzoylamino-3,4-dihydrocarbostyril
8. 6-(2-Methoxybenzoyl)amino-3,4-dihydrocarbostyril
9. 6-(3,4-Methylenedioxybenzoyl)amino-3,4-dihydrocarbostyril
10. 6-Thiobenzoylamino-3,4-dihydrocarbostyril.½hydrate
11. 6-(N,N-Dimethylureido)-3,4-dihydrocarbostyril
12. 6-Ureido-3,4-dihydrocarbonstyril

TABLE 2

| Test Comp. No. | Dose (mole) | Change of contraction of ventricle muscle (Change %) | Change of blood flow volume in coronary artery (ml/min.) |
|---|---|---|---|
| 1 | 1 | 35 | 2.0 |
| 2 | 1 | 13 | 1.25 |
| 3 | 1 | 59 | 3.5 |
| 4 | 1 | 61 | 3.7 |
| 5 | 1 | 102 | 3.75 |
| 6 | 1 | 60 | 7.8 |
| 7 | 0.3 | 18 | 2.5 |
| 8 | 0.1 | 8 | 2.5 |
| 9 | 0.3 | 13 | 2.0 |
| 10 | 0.1 | 3 | 1 |
| 11 | 1 | 35 | 1.75 |
| 12 | 1 | 9 | 0.5 |
| Amrinone | 1 | 27 | — |

| Preparation 1 | |
|---|---|
| Components | Amount in a tablet |
| 6-Ethoxycarbonylamino-3,4-dihydrocarbostyril | 5 mg |
| Starch | 132 mg |
| Magnesium stearate | 18 mg |
| Lactose | 45 mg |
| Totally | 200 mg |

The above components are tabletted in a usual manner to give tablets containing the above amounts of the components in each one tablet.

| Preparation 2 | |
|---|---|
| Components | Amount in a tablet |
| 6-Methylthiocarbonylamino-3,4-dihydrocarbostyril | 10 mg |
| Starch | 127 mg |
| Magnesium stearate | 18 mg |
| Lactose | 45 mg |
| Totally | 200 mg |

The above components are tabletted in a usual manner to give tablets containing the above amounts of the components in each tablet.

| Preparation 3 | |
|---|---|
| Components | Amount in an injection |
| 6-Ethoxycarbonylamino-3,4-dihydrocarbostyril | 500 mg |
| Polyethylene glycol | 0.3 g |
| Sodium chloride | 0.9 g |
| Polyoxyethylene sorbitan monooleate | 0.4 g |
| Sodium metabisulfite | 0.1 g |
| Methyl parabene | 0.18 g |
| Propyl parabene | 0.02 g |
| Distilled water for injection | (total) 100 ml |

The above parabenes, sodium metabisulfite and sodium chloride are dissolved with stirring in the above distilled water at 80° C. The resulting solution is cooled to 40° C., and therein are dissolved the compound of the present invention and then polyethylene glycol and polyoxyethylene sorbitan monooleate. To the solution is added distilled water for injection so as to become totally 100 ml. The solution is sterilized by filtering with a filter paper, and then each 1 ml is poured into an ampoule to give an injection.

| Preparation 4 | |
|---|---|
| Components | Amount in a tablet |
| 6-Phenoxycarbonylamino-3,4-dihydrocarbostyril | 5 mg |
| Starch | 132 mg |
| Magnesium stearate | 18 mg |
| Lactose | 45 mg |
| Totally | 200 mg |

The above components are tabletted in a usual manner to give tablets containing the above amounts of the components in each tablet.

What is claimed is:
1. A carbostyril compound of the formula:

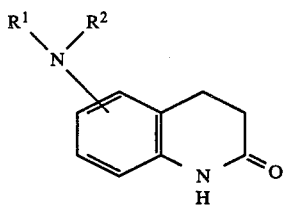 (1)

wherein R¹ is hydrogen atom or a lower alkyl group, R² is a lower alkyl group or a group of the formula:

R³ is a lower alkylthio group, a lower alkyl group, a lower alkoxy group, phenoxy group, a phenyl(lower)alkoxy group, a lower alkenyloxy group, a phenyl group which may have a substituent selected from a lower alkoxy and a lower alkylenedioxy group on the phenyl ring, or a group of the formula: —NR⁴R⁵ (R⁴ and R⁵ are the same or different and are each hydrogen atom or a lower alkyl group), and X is oxygen atom or sulfur atom, provided that when R¹ is hydrogen atom and R² is the group of the formula:

X is not oxygen atom and R³ is not a lower alkyl group, and a pharmaceutically acceptable salt thereof.

2. The carbostyril compound according to claim 1, wherein R³ is an alkylthio having 1 to 6 carbon atoms or an alkoxy having 1 to 6 carbon atoms, and X is sulfur atom.

3. The carbostyril compound according to claim 1, wherein R³ is an alkylthio having 1 to 6 carbon atoms or an alkoxy having 1 to 6 carbon atoms, and X is oxygen atom.

4. The carbostyril compound according to claim 1, wherein R³ is phenoxy, a phenylalkoxy having 1 to 6 carbon atoms in the alkoxy moiety, an alkenyloxy having 2 to 6 carbon atoms, or a group of the formula: —NR⁴R⁵ (R⁴ and R⁵ are the same or different and are each hydrogen atom or an alkyl having 1 to 6 carbon atoms), and X is sulfur atom or oxygen atom.

5. The carbostyril compound according to claim 1, wherein R³ is an alkyl having 1 to 6 carbon atoms or a phenyl group which may have a substituent selected from an alkoxy having 1 to 6 carbon atoms or an alkylenedioxy having 1 to 4 carbon atoms, and X is sulfur atom or oxygen atom.

6. The carbostyril compound according to claim 5, wherein R³ is an alkyl having 1 to 6 carbon atoms.

7. The carbostyril compound according to claim 1, wherein the substituent: —NR¹R² is substituted at 6-position.

8. The carbostyril compound according to claim 7, wherein R² is a group of the formula:

in which R³ is an alkylthio having 1 to 6 carbon atoms or an alkoxy having 1 to 6 carbon atoms, and X is sulfur atom or oxygen atom.

9. The carbostyril compound according to claim 1, which is methyl(3,4-dihydrocarbostyril-6-yl)-dithiocarbamate.

10. The carbostyril compound according to claim 1, which is 6-ethoxycarbonylamino-3,4-dihydrocarbostyril.

11. The carbostyril compound according to claim 1, which is 6-methoxycarbonylamino-3,4-dihydrocarbostyril.

12. The carbostyril compound according to claim 1, which is 6-(N-methyl-N-isobutoxycarbonylamino)-3,4-dihydrocarbostyril.

13. A cardiotonic composition, which comprises as an essential active ingredient a carditonic effective amount of a carbostyril compound of the formula:

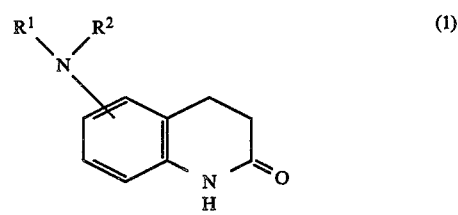 (1)

wherein R¹ is hydrogen atom or a lower alkyl group, R² is a lower alkyl group or a group of the formula:

R³ is a lower alkylthio group, a lower alkyl group, a lower alkoxy group, phenoxy group, a phenyl(lower)alkoxy group, a lower alkenyloxy group, a phenyl group which may have a substituent selected from a lower alkoxy and a lower alkylenedioxy group on the phenyl ring, or a group of the formula: —NR⁴R⁵ (R⁴ and R⁵ are the same or different and are each hydrogen atom or a lower alkyl group), and X is oxygen atom or sulfur atom, provided that when R¹ is hydrogen atom and R² is the group of the formula:

X is not oxygen atom and R³ is not a lower alkyl group, or a pharmaceutically acceptable salt thereof in admixture with a conventional carrier or diluent.

14. A method for the treatment of congestive heart failure, which comprises administering an effective amount of a carbostyril compound of the formula:

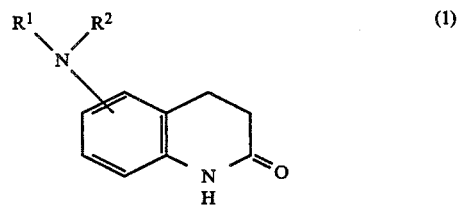 (1)

wherein R¹ is hydrogen atom or a lower alkyl group, R² is a lower alkyl group or a group of the formula:

$R^3$ is a lower alkylthio group, a lower alkyl group, a lower alkoxy group, phenoxy group, a phenyl(lower)alkoxy group, a lower alkenyloxy group, a phenyl group which may have a substituent selected from a lower alkoxy and a lower alkylenedioxy group on the phenyl ring, or a group of the formula: —$NR^4R^5$ ($R^4$ and $R^5$ are the same or different and are each hydrogen atom or a lower alkyl group), and X is oxygen atom or sulfur atom, provided that when $R^1$ is hydrogen atom and $R^2$ is the group of the formula:

X is not oxygen atom and $R^3$ is not a lower alkyl group, or a pharmaceutically acceptable salt thereof to patients suffering from congestive heart failure.

15. The carbostyril compound according to claim 1, wherein $R^1$ is a hydrogen atom or an alkyl having 1 to 6 carbon atoms, $R^2$ is a group of the formula:

$R^3$ is an alkylthio having 1 to 6 carbon atoms, an alkyl having 1 to 6 carbon atoms, an alkoxy having 1 to 6 carbon atoms, phenoxy, a phenylalkoxy having 1 to 6 carbon atoms in the alkoxy moiety, an alkenyloxy having 2 to 6 carbon atoms, or a phenyl which may have a substituent selected from an alkoxy having 1 to 6 carbon atoms and an alkylenedioxy having 1 to 4 carbon atoms on the phenyl ring, and X is oxygen atom or sulfur atom, provided that when $R^1$ is hydrogen atom, $R^3$ is not an alkyl having 1 to 6 carbon atoms and X is not oxygen atom, and a pharmaceutically acceptable salt thereof.

16. The carbostyril compound according to claim 2, wherein $R^3$ is an alkylthio having 1 to 6 carbon atoms.

17. The cardiotonic composition according to claim 13, wherein $R^1$ is hydrogen atom or an alkyl having 1 to 6 carbon atoms, $R^2$ is a group of the formula:

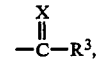

$R^3$ is an alkylthio having 1 to 6 carbon atoms, an alkyl having 1 to 6 carbon atoms, an alkoxy having 1 to 6 carbon atoms, phenoxy, a phenylalkoxy having 1 to 6 carbon atoms in the alkoxy moiety, an alkenyloxy having 2 to 6 carbon atoms, or a phenyl which may have a substituent selected from an alkoxy having 1 to 6 carbon atoms and an alkylenedioxy having 1 to 4 carbon atoms on the phenyl ring, and X is oxygen atom or sulfur atom, provided that when $R^1$ is hydrogen atom, $R^3$ is not an alkyl having 1 to 6 carbon atoms and X is not oxygen atom, and a pharmaceutically acceptable salt thereof.

* * * * *